(12) United States Patent
Herrmann

(10) Patent No.: US 9,268,035 B2
(45) Date of Patent: Feb. 23, 2016

(54) SPECTRAL PHOTON COUNTING DETECTOR

(71) Applicant: KONINKLIJKE PHILIPS N.V., Eindhoven (NL)

(72) Inventor: Christoph Herrmann, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/408,097

(22) PCT Filed: Jun. 26, 2013

(86) PCT No.: PCT/IB2013/055237
§ 371 (c)(1),
(2) Date: Dec. 15, 2014

(87) PCT Pub. No.: WO2014/002022
PCT Pub. Date: Jan. 3, 2014

(65) Prior Publication Data
US 2015/0185332 A1    Jul. 2, 2015

Related U.S. Application Data

(60) Provisional application No. 61/664,984, filed on Jun. 27, 2012.

(51) Int. Cl.
*G01J 5/02* (2006.01)
*G01T 1/17* (2006.01)
(Continued)

(52) U.S. Cl.
CPC ............... *G01T 1/171* (2013.01); *G01N 23/046* (2013.01); *H03M 1/125* (2013.01)

(58) Field of Classification Search
CPC ......... G01J 5/02; G01T 1/171; G01N 23/046; H03M 1/125
See application file for complete search history.

(56) References Cited

U.S. PATENT DOCUMENTS 5,821,533 A    10/1998 Bingham et al.
5,844,514 A *  12/1998 Ringh et al. ............... 341/143
(Continued)

FOREIGN PATENT DOCUMENTS

GB    2332513 A    6/1999
WO    2008155679 A2    12/2008
WO    2009050619 A2    4/2009

OTHER PUBLICATIONS

Engel et al: A Multi-Channel Integrated Circuit for Use in Low-And Intermediate-Energy Nuclear Physics—HINP16C; Nuclear Instruments and Methods in Physics Research A, vol. 573, 2007, pp. 418-426.

(Continued)

*Primary Examiner* — David Porta
*Assistant Examiner* — Faye Boosalis

(57) ABSTRACT

An apparatus includes a pulse shaper (120) for receiving signals indicative of detected photons and generating a plurality of pulses therefrom to form a pulse train (200) and a peak detector (150) for sampling the pulse train (200) at an output of the pulse shaper (120). The peak detector (150) includes a circuit (300) for selectively detecting and sampling a maximum (202a, b, c) and a minimum (204a, b) value of the pulse train (200). The maximum (202a, b, c) and minimum (204a, b) values sampled are then converted from analog-to-digital format via an analog-to-digital converter (160).

20 Claims, 6 Drawing Sheets

(51) Int. Cl.
*G01N 23/04* (2006.01)
*H03M 1/12* (2006.01)

(56) References Cited

U.S. PATENT DOCUMENTS

| 7,924,207 | B2 | 4/2011 | Snoeij et al. | |
|---|---|---|---|---|
| 8,338,791 | B2 * | 12/2012 | Proksa et al. | 250/369 |
| 2006/0033650 | A1 * | 2/2006 | Leung et al. | 341/143 |
| 2009/0259709 | A1 * | 10/2009 | Nikitin | 708/801 |
| 2011/0036989 | A1 | 2/2011 | Marks et al. | |
| 2012/0027274 | A1 | 2/2012 | Farahani et al. | |

OTHER PUBLICATIONS

Lee et al: "Design of a 1.8V 8-Bit 1GSPS Cascaded-Folding CMOS A/D Converter Based on a Folder Averaging Technique"; IEEE International Soc Conference, 2009, pp. 79-82.

* cited by examiner

SPECTRAL PHOTON COUNTING DETECTOR

CROSS-REFERENCE TO PRIOR APPLICATIONS

This application is the U.S. National Phase application under 35 U.S.C. §371 of International Application No. PCT/IB2013/055237, filed on Jun. 26, 2013, which claims the benefit of U.S. Provisional Patent Application No. 61/664,984, filed on Jun. 27, 2012. These applications are hereby incorporated by reference in their entirety herein.

The present application generally relates to spectral photon counting detectors. While it is described with particular application to computed tomography (CT), it also relates to other applications in which it is desirable to energy-resolve detected photons having different energies.

A computed tomography (CT) system includes a radiation source that emits poly-energetic ionizing photons that traverse an examination region. Such a system also includes a radiation sensitive detector, located opposite the examination region from the radiation source that detects the photons that traverse the examination region. The detector produces an electrical signal, such as a current or voltage, for each detected photon. The detector further includes electronics for energy-resolving the detected photons based on the electrical signals.

By way of example, a radiation sensitive detector includes a pulse shaper for processing an electrical current produced by a sensor to generate a voltage pulse having a peak amplitude indicative of the energy of the detected photon. The detector also includes a discriminator that compares the amplitude of the voltage pulse with two or more thresholds that are set in accordance with different energy levels. The output of the discriminator for a first threshold goes high when the pulse amplitude increases and crosses the first threshold and low when the pulse amplitude decreases and crosses a second threshold. For each of the first and second thresholds, a counter counts the rising edges. When two or more thresholds and corresponding counters are incorporated in the detector, an energy binner can energy-bin the counts in energy ranges or bins. Therefore, the detected photons are energy resolved based on the binned data.

Unfortunately, the time between successive photon detections may result in pulse pile-up within the sensor or the pulse shaper generates pulses that overlap. When pulses overlap, their amplitudes may combine so that the individual pulses are not readily discernable from the combination. As a consequence, the discriminator may not see the amplitude of a pulse cross a given threshold. In addition, the peak energy of a pulse may be shifted by the amplitude contribution of overlapping pulses. As a result, the energy distribution of the detected photons may be erroneously shifted.

Moreover, in photon-counting energy-resolving detectors, at higher X-ray flux, pile-up of pulses at the output of the shaper results, because the shaper pulse duration is too long to separate between adjacent distinguishable pulses coming from the direct converting sensor. Due to pile-up, the energy estimation derived from comparing the shaper output with a number of different discriminator thresholds becomes wrong. Stochastic models have been proposed to incorporate pile-up into the maximum likelihood evaluation scheme, however, this approach does not result in a much improved energy estimation, since the space of possible solutions is so large that the probability of the most likely solution does not differ considerably from that of the least likely solution.

Conventional photon-counting readout circuits use a small number of discriminators to coarsely estimate the height of the pulses generated by the preceeding shaper. As soon as pile-up comes into play, the pulse heights are no longer determined correctly.

Aspects of the present application address the above-referenced matters and others.

According to one aspect, an apparatus includes a pulse shaper for receiving signals indicative of detected photons and generating a plurality of pulses therefrom to form a pulse train and a peak detector for sampling the pulse train at an output of the pulse shaper. The peak detector includes a circuit for selectively detecting and sampling local maximum and minimum values of the pulse train. The maximum and minimum values sampled are then converted from analog-to-digital format via an analog-to-digital converter.

In another aspect, a method includes receiving signals indicative of detected photons, via a pulse shaper, generating a plurality of pulses therefrom to form a pulse train, sampling the pulse train at an output of the pulse shaper, via a peak detector and selectively detecting and sampling maximum and minimum values of the pulse train, via a circuit in the peak detector.

Still further aspects of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 1:
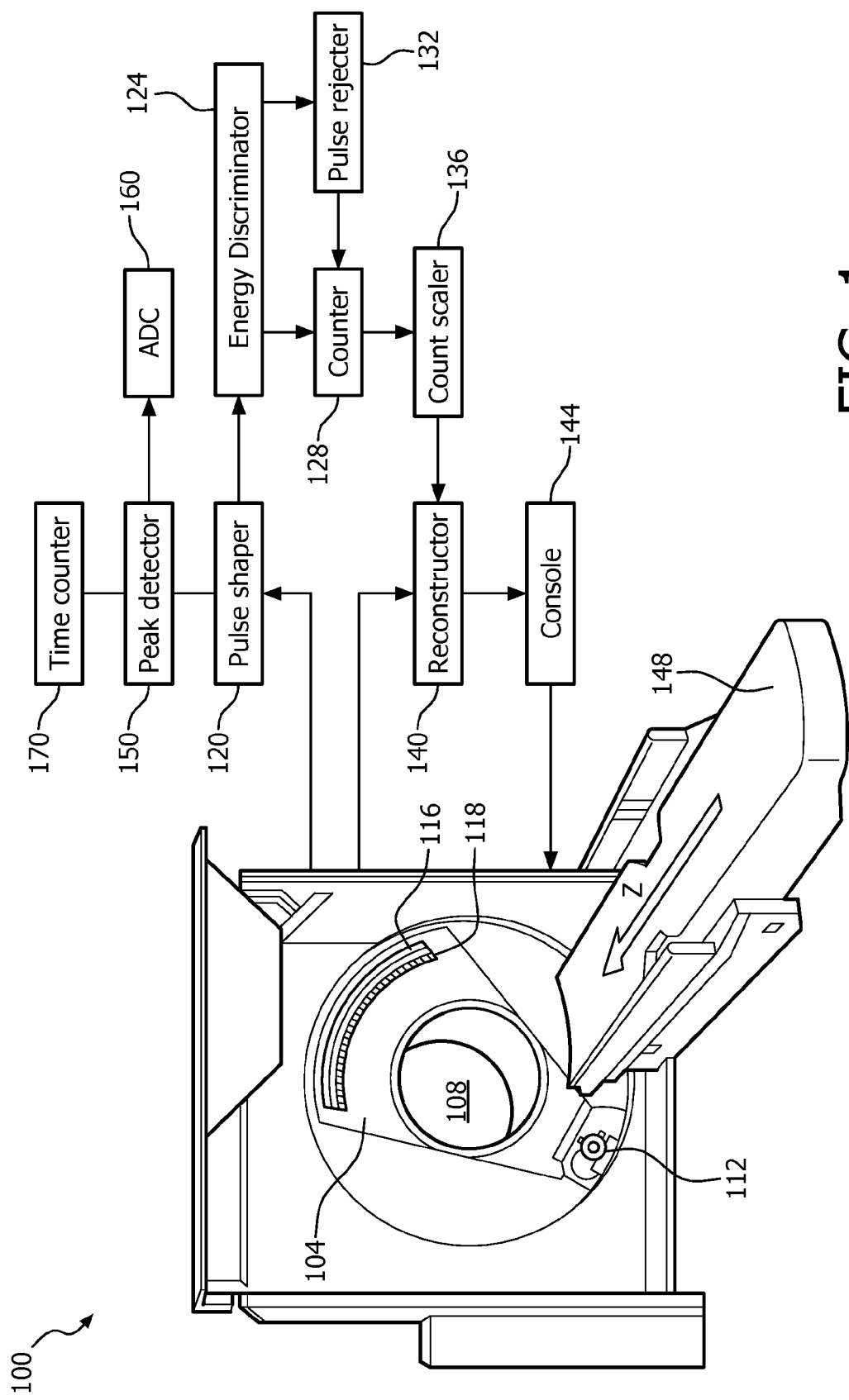
FIG. 1 illustrates an example of an imaging system.

With reference to FIG. 1, a computed tomography (CT) system 100 includes a rotating gantry portion 104, which rotates about an examination region 108 around a longitudinal or z-axis. An x-ray source 112, such as an x-ray tube, is supported by the rotating gantry portion 104 and emits a poly-energetic radiation beam that traverses the examination region 108.

A radiation sensitive detector 116 includes a plurality of pixels 118 that detect photons emitted by the source 112 over at least one hundred and eighty degrees, plus a fan angle. Each of the plurality of pixels 118 generates a corresponding electrical signal, such as electrical currents or voltages, for each detected photon. Examples of suitable sensors include direct conversion detectors (e.g., cadmium zinc telluride (CZT) based detectors) and scintillator-based sensors that include a scintillator in optical communication with a photosensor.

A pulse shaper 120 processes the electrical signals and generates one or more pulses, such as voltage or other pulses indicative of the detected photon. The pulse shaper 120 may include electronics for integrating charge during a first time interval to produce pulses with peak amplitudes indicative of the energy of the detected photons and electronics for integrating the charge during a second, relatively shorter time interval to produce pulses with peak amplitudes indicative of whether the energy of a detected photon exceeds a minimum desired energy.

An energy discriminator 124 energy-discriminates the pulses. This includes comparing the amplitudes of the generated pulses with one or more thresholds that respectively correspond to particular energy levels. The energy discriminator 124 produces an output signal, for each threshold, indicative of whether the amplitude increases and crosses the corresponding threshold and decreases and crosses the threshold. For instance, the output signal may include rising (or falling) edges when the amplitude increases and crosses the corresponding threshold and falling (or rising) edges when the amplitude decreases and crosses the corresponding threshold.

A counter 128 counts the rising (or falling) edges in the signals for each threshold. A pulse rejecter 132 rejects pulses, or gates the counter 128 so that the counter 128 disregards or otherwise does not count the rising (or falling) edges for undesired pulses such as piled-up pulses. The pulse rejecter 132 produces a gating signal based on the output of the energy discriminator 124.

A count scaler 136 scales or otherwise adjusts the count for the thresholds to account for disregarded pulses, which are not counted.

A reconstructor 140 selectively reconstructs the signals generated by the detector 116 based on the spectral characteristics of the signals.

An object support 148, such as a couch, supports a patient or other object in the examination region 108. The object support 148 is movable so as to guide the object with respect to the examination region 108 when performing a scanning procedure.

A general purpose computer serves as an operator console 144. The console 144 includes a human readable output device, such as a monitor or display, and an input device, such as a keyboard and mouse. Software resident on the console 144 allows the operator to control and interact with the scanner 100, for example, through a graphical user interface (GUI). Such interaction may include instructions for reconstructing the signals based on the spectral characteristics.

To further improve the measurement result, it may be possible to run a time counter 170 in each pixel, which records, for example, in the form of a bit string, that is, one bit for each clock cycle, a "1" designation representing a detected maximum or minimum, at which point in time a minimum or a maximum was detected. The time counter 170 may be connected to a peak detector 150 for counting the time between a maximum 202*a, b, c* and a minimum 204*a, b* value of a pulse train 200 (see FIG. 2 described below) in order to get an improved timing between the maxima and minima (the original pulse train is characterized by the set of minima and maxima and the time distance between a maximum and the adjacent minimum). The peak detector 150 may also communicate with an analog-to-digital converter 160, as will be described further below.

Moreover, the time counter 170 refers to the number of clock ticks (e.g., for a 10 MHz clock) within a pre-defined measurement period (e.g., 100 µs) resulting in e.g., 1000 clock ticks per measurement period. Whenever a maximum or a minimum is detected, the time counter 170 generates a "1" for the time clock tick, during which the maximum or minimum was detected, while any other clock tick is assigned the value "0". The resulting bit string of "0s" and "1s" is read out during the following measurement period (this also needs at least a readout clock speed of 10 MHz) and then used together with the set of maxima and minima to reconstruct the original pulse train using the improved timing between maxima and minima. Alternatively, the time counter 170 may also be implemented as a read counter, which starts at 0 when a maximum (or minimum) is detected and is incremented until the following minimum (or maximum) is detected, in which case the counter value is latched, and counting can restart. Then, however, as many latches are needed as there are pairs of maxima and minima possible within the measurement period.

As discussed above, the output of the pulse shaper 120 is sampled at a very high frequency in order to reconstruct the correct pulse heights of the pulse train 200, which shows pile-up of pulses.

Figure 2:
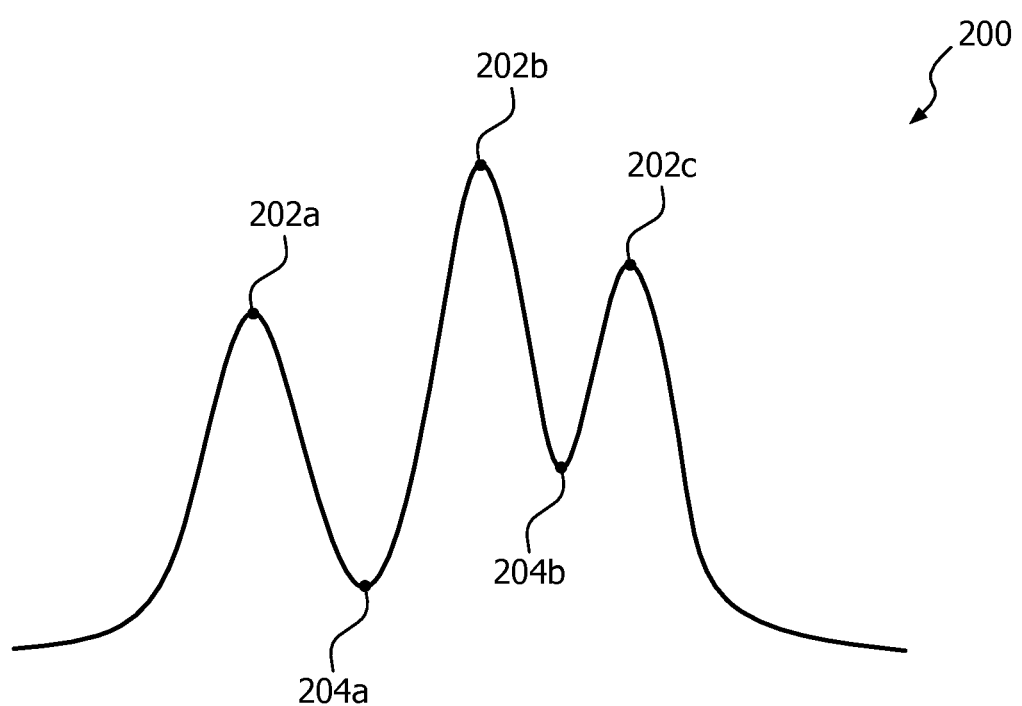
FIG. 2 illustrates an example of a valley and hill (minima and maxima) pulse train.

With reference to FIG. 2, in order to reduce pulse pileup, the following approach is proposed, which provides a means to reconstruct the full pulse train 200 without sampling the shaper output at a very high sampling frequency. Since the shaper output, as implemented in any photon-counting ASIC for spectral computing tomography, results in "valley and hill" waveforms, in which the hills identify the pulse maximum, and the valleys represent a (possibly incomplete) return to the baseline, a circuit 300 with an analog maximum detector and an analog minimum detector (see FIG. 3, described below), both derived from a peak detector 150 (see FIG. 1), is used to sample the pulse train 200 at the output of the pulse shaper 120, only at the maxima and minima (see FIG. 2). The sampled values are then analog-to-digitally converted via an ADC 160 (see FIG. 1).

Given the sequence of local maxima and minima, it is then possible to reconstruct the actual pulse train 200 using a model for the shaper output, which may be obtained from test-pixel measurements or from CMOS circuit simulations. As a result, a relatively accurate estimate of the complete pulse train 200 is obtained in which pile-up effects are visible and hence can fully be corrected for, as long as two pulses are not exactly on top of each other, so that their superposition cannot be detected at all.

Moreover, it is contemplated that the time counter 170 (see FIG. 1) may be configured to communicate with a storage unit (not shown) for transferring and storing the maximum 202*a, b, c* and minimum 204*a, b* values of the pulse train 200, locally or remotely. For example, "store signals" may be transmitted to any type of storage circuit. The combination of the time count and the data count provides time-based digital information representative of the pulse train(s) received from the pulse shaper 120. With this information, it becomes possible to accurately reconstruct the "valley-and-hill" type pulse train 200.

FIG. 2 shows an example of the valley-and-hill waveform 200, which is usually generated by the superposition of pulses of different heights shifted in time relative to each other. The pulse shapes are determined by the pulse shaping circuit 300 (see FIG. 3), which is used for processing the current pulses, which are generated by the direct conversion crystal.

Thus, by sampling the local maxima 202*a, b, c* and the local minima 204*a, b*, and analog-to-digitally converting them (see FIGS. 1 and 3), it is possible to reconstruct the original set of individual pulses including their correct energy, if an estimate of the pulse shape as generated by a shaping amplifier (not shown) is available.

Figure 3:
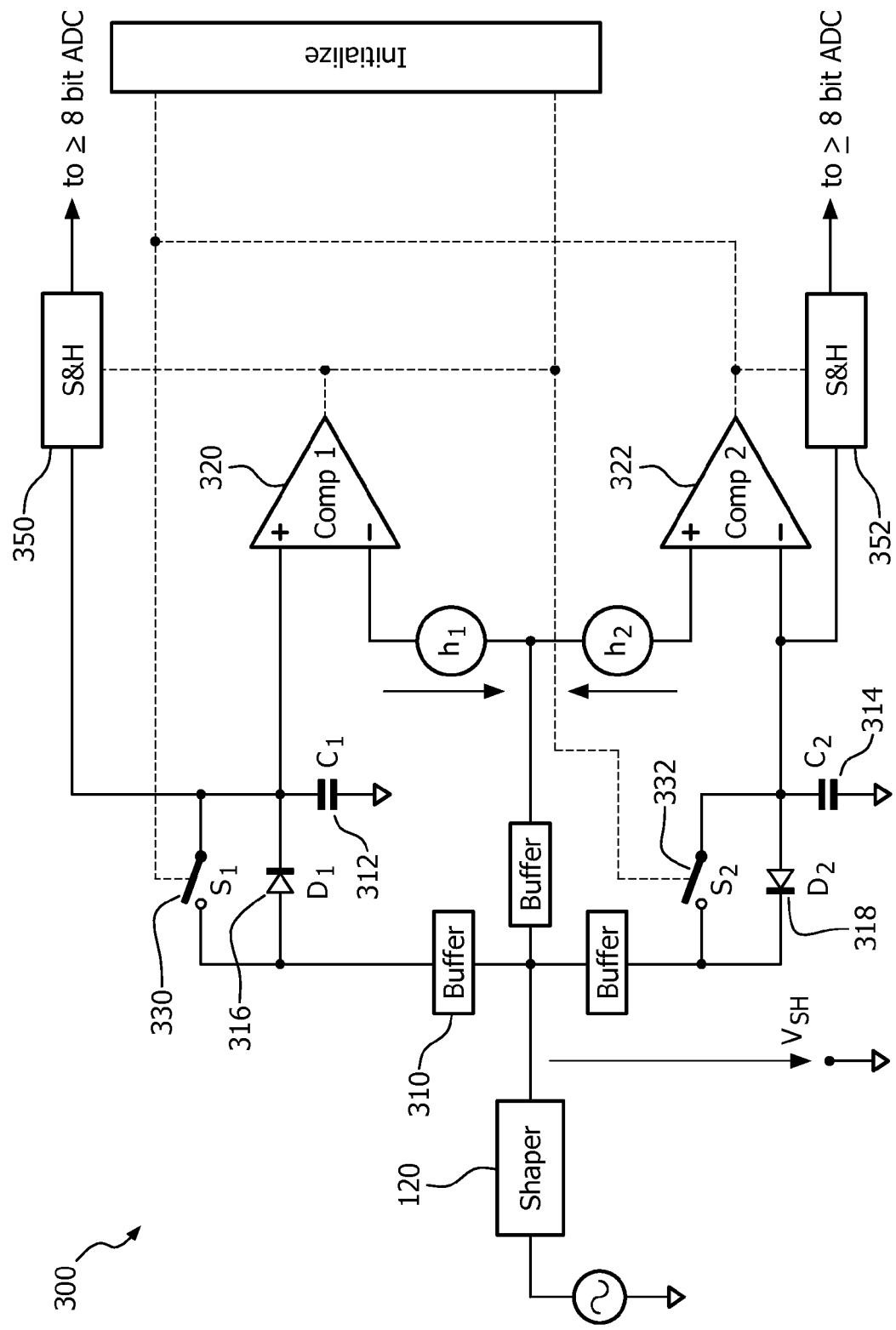
FIG. 3 illustrates an example of a circuit for detecting local maxima and minima.

FIG. 3 shows a circuit implementation 300, where the elements described below are electrically connected to each other, directly or indirectly, for detecting local maxima and local minima, as shown in FIG. 2. In operation, initially, a first switch 330 ($S_1$) and a second switch 332 ($S_2$) are closed so that first and second capacitors 312, 314 ($C_1$ and $C_2$) store the baseline at the output of the pulse shaper 120. To start the operation, the first switch 330 and the second switch 332 are opened.

As shown in FIG. 3, when the shaper output increases, a second diode 318 ($D_2$) blocks so that the second capacitor 314 ($C_2$) keeps the baseline potential, while a first diode 316 ($D_1$) conducts, and the first capacitor 312 ($C_1$) follows the voltage at the output of the pulse shaper 120. This changes, if the first local maximum of the shaper output waveform, $V_{SH}$, is reached and passed. From then on, the shaper output voltage is smaller than the voltage $V(C_1)$ across the first capacitor 312, $C_1$, so that the first diode 316 ($D_1$) stops conducting, and the voltage across the first capacitor 312 ($C_1$) is frozen. Only if $V_{SH}$ becomes, by $h_1$, smaller than $V(C_1)$ (i.e., $V_{SH}+|h_1|=V(C_1)$), the first comparator 320 (Comp1) trips (minus-plus transition), and causes:

(i) $V(C_1)$ to be sampled and analog-to-digitally converted and (ii) closure of the second switch 332 ($S_2$) for a short time, so that the second capacitor 314 ($C_2$) can be charged to $V_{SH}$ at that point in time.

$h_1$ is a hysteresis value used to avoid wrongly sampling the true maximum (minimum) due to noise on top of the voltage waveform $V_{SH}$ at the output of the pulse shaper 120.

Additionally, an output of the first comparator 320 is received by a first sample and hold (S&H) block 350, whereas an output of the second comparator 322 is received by a second sample and hold (S&H) block 352.

From then on, $V(C_1)$ is frozen, and $V(C_2)$ follows $V_{SH}$, since the second diode 318 ($D_2$) conducts, until $V_{SH}$ reaches a local minimum, from which point in time on, the second diode 318 ($D_2$) starts to block, so that $V(C_2)$ is kept frozen. As soon as $V_{SH}$ becomes, by $h_2$, larger than $V(C_2)$ (i.e., $V_{SH}-|h_2|=V(C_2)$), the second comparator 322 (Comp2) trips (minus-plus transition), and now causes:

(i) $V(C_2)$ to be sampled and analog-to-digitally converted and (ii) closure of the first switch 330 ($S_1$) for a short time, so that the first capacitor 312 ($C_1$) can be charged to $V_{SH}$ at that point in time, so that this branch is then ready to process the next maximum.

$h_2$ is a hysteresis value used to avoid wrongly sampling the true maximum (minimum) due to noise on top of the voltage waveform $V_{SH}$ at the output of the pulse shaper 120.

Figure 4:
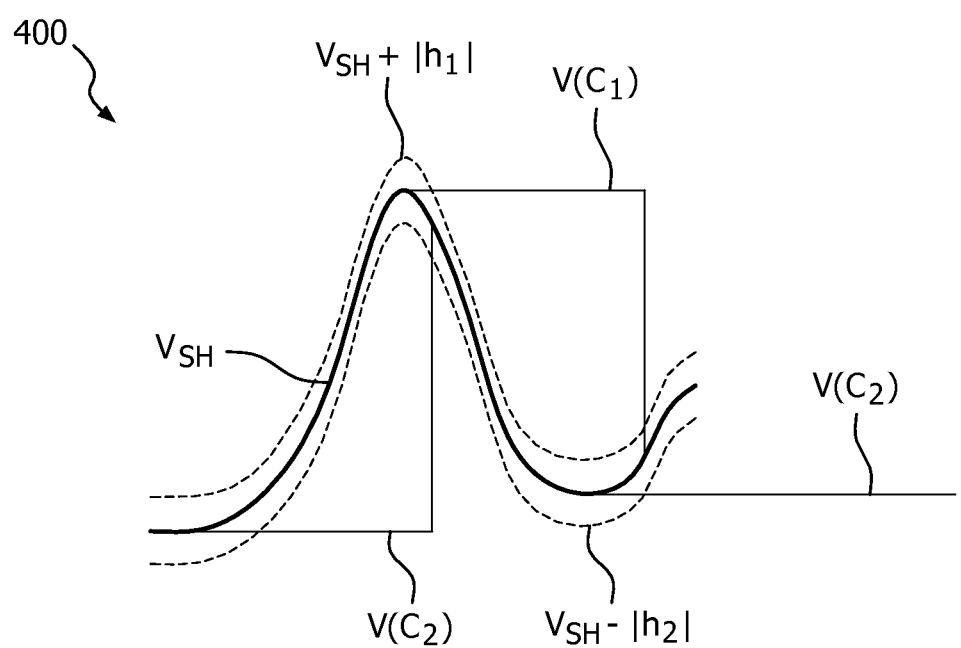
FIG. 4 illustrates an example of a time behavior for $V_{SH}$, $V_{(C1)}$, and $V_{(C2)}$.

This procedure is illustrated in FIG. 4, depicting a time behavior 400 for $V_{SH}$, $V_{(C1)}$, and $V_{(C2)}$.

The above approach is much less power-consuming than just sampling the analog pulse, for example, with 1 GHz (ins sampling period) and analog-to-digitally converting each sample. Still implementation has to be optimized to meet low power requirements, such as, for example, 3 mW per pixel.

Moreover, in view of the fact that Poissonian arrivals show interarrival times, which can be shorter or longer than the mean arrival rate, some buffering of the sampled local maxima or minima is helpful to deal with phases of interarrival times, which are shorter than the mean arrival rate. Such buffering means 310 (see FIG. 3) indicates that, per pixel, a number of additional N capacitors are used, in which a sampling value is stored until it can be analog-to-digitally converted. Hence, a high-speed analog-to-digital (ADC) 160 may be used (see FIG. 1), which serves a larger number of pixels.

Thus, it is possible to design a 1 GHz 8 bit ADC with only 200 mW power consumption. Assuming a mean photon arrival rate of 5 Mcps per pixel, this means that the ADC can serve: 1 GHz/(2×5 MHz)=100 pixels, so that the power consumption per pixel for analog-to-digital conversion is 2 mW. In one exemplary embodiment, where an M/D/1 queueing system may apply, serving 100 pixels at 5 MHz with a Poisson input of 5Mcps corresponds to an offered traffic value $\rho=1$, which results in a queue building up to infinity, if the number of buffer places were unlimited.

However, for an offered traffic value of $\rho=0.8$, with a probability of 1.1e–3 (:=1.1×10$^{-3}$) the queue length equals 14, and the probability of having more than 14 events in this queue (so that one would lose events, if there were only N=14 buffer places) is about 2.1e–3, i.e., the probability of losing events is less than or equal to this number.

This requires an ADC sampling rate of 6.25 MHz ($\rho=0.8=5$ Mcps6.25 MHz), which then gives a power consumption per pixel of 200 mW/(1 GHz(2×6.25 MHz))=2.5 mW with the ADC.

Since a single ADC serves 80 pixels (1 GHz(2×6.25 MHz)), the loss probability may be even lower, since there are usually pixels, which see a lower arrival rate (well-known "bundling gain") so that the ADC 160 can serve other pixels with higher arrival rates.

Figure 5:
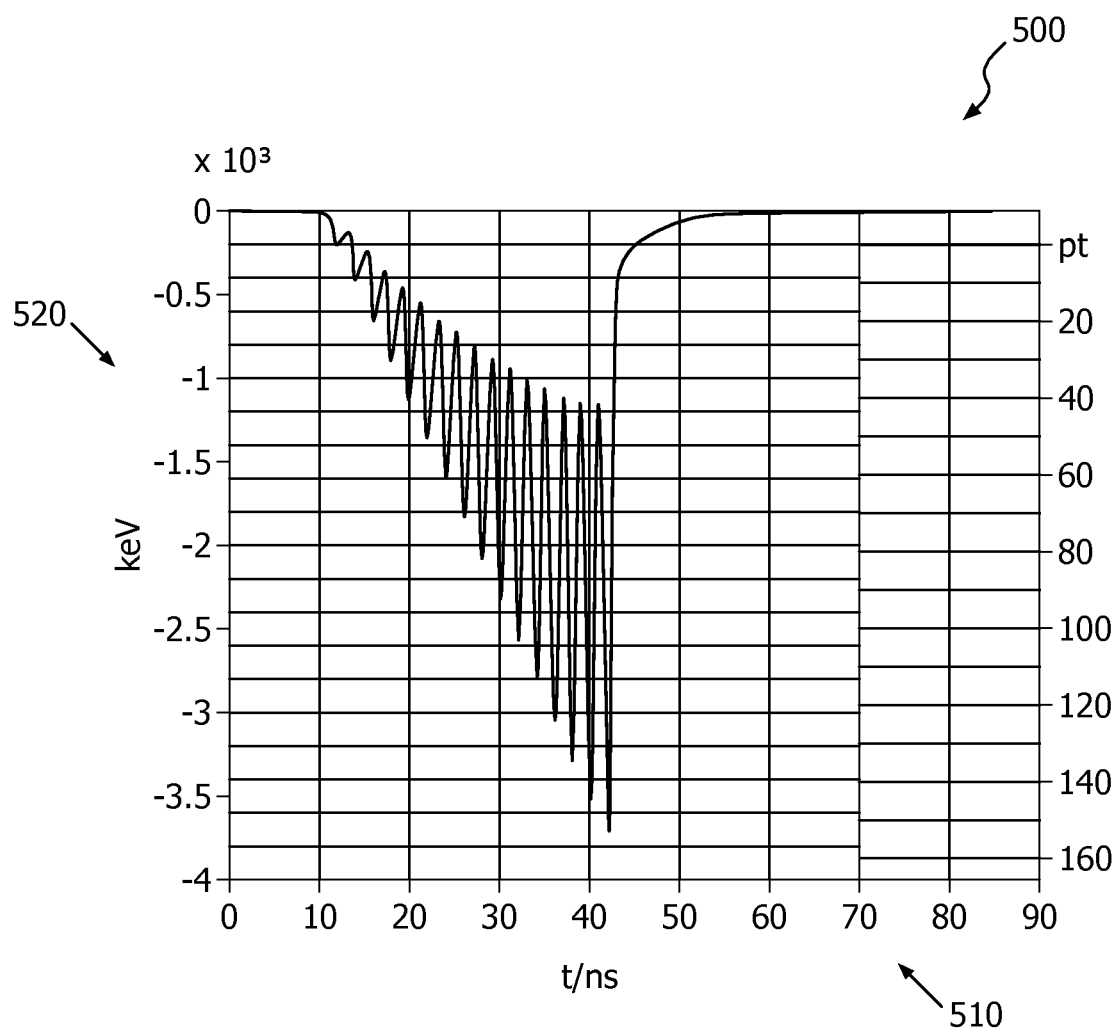
FIG. 5 illustrates an example of a pulse train resulting from shaper waveforms with 2 ns distance.

Thus, with the above approach, it is possible to support an incident count rate of 5 Mcps/pixel without any error due to pile-up, since pile-up can be fully reconstructed from the "hill-and-valley" pulse train 200. Correct energy information can be obtained, if the minimum before each maximum is known, and by using the pulse shape waveforms known from the pulse shaper 120. This is illustrated in FIG. 5, where pulse train 500 is depicted resulting from shaper waveforms with 2 n distance. The x-axis 510 illustrates time, whereas the y-axis 520 illustrates voltage. In FIG. 5, where negative pulses are assumed, i.e., local minima and maxima have to be exchanged for each other. With the local maxima known, it is possible to correctly quantize the true pulse height from corresponding local minimum.

Furthermore, if a minimum equals the baseline, the correct pulse height can directly be obtained from the next maximum following this minimum. The baseline can be sampled at the beginning of the operation and stored in a third capacitor ($C_3$) (not shown in FIG. 3).

With an 8 bit ADC, the quantization error (formula for an equally distributed random variable) is, for example: stepsize/sqrt(12)=140 keV/(256*sqrt(12))=0.1578 keV.

Noise characterization can be performed as follows:

Generate, for example, 1000 test pulses of defined energy and determine the rms-value from the analog-to-digitally converted amplitude.

Figure 6:
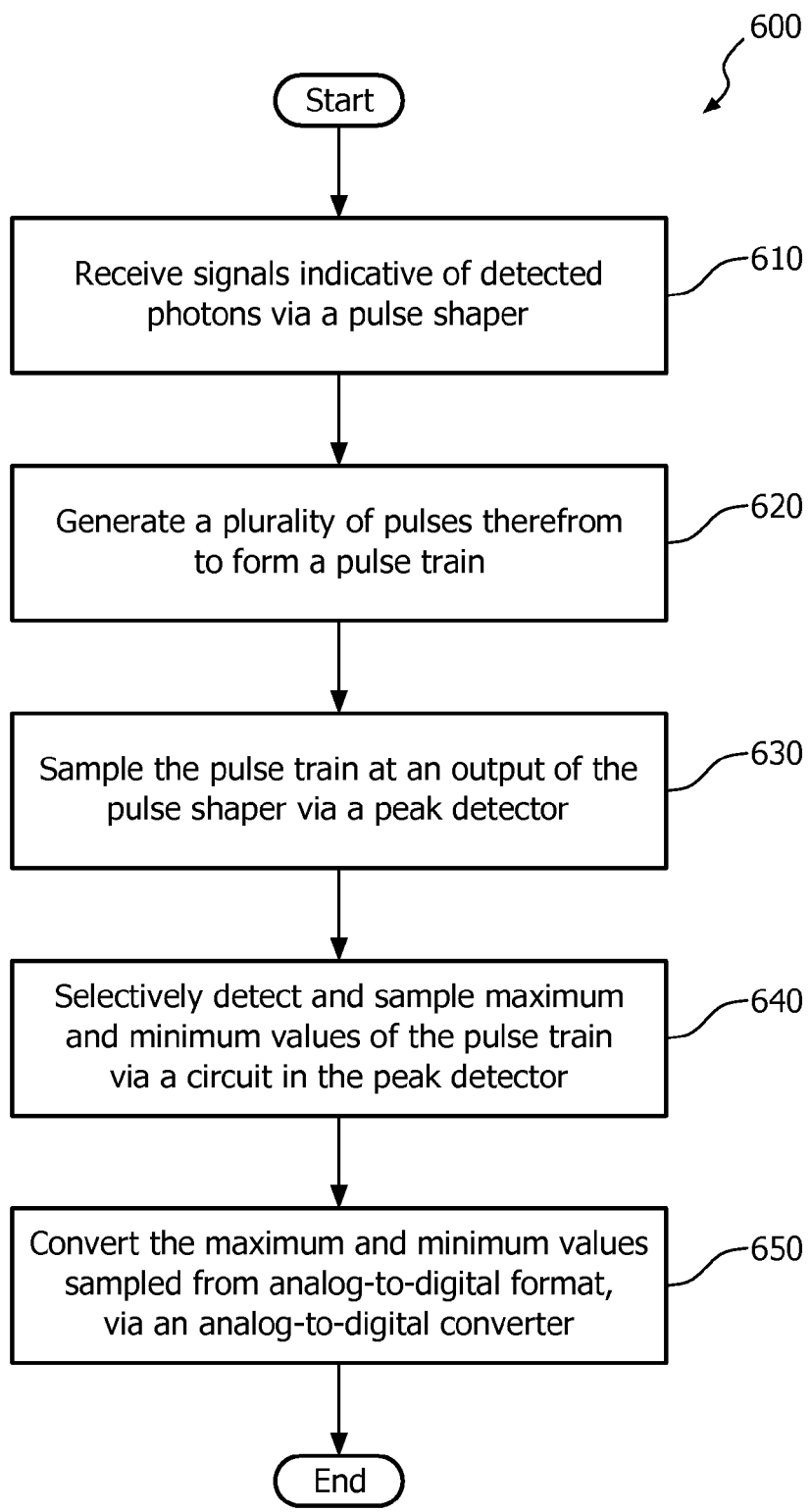
FIG. 6 illustrates an example of a flowchart of a method for photon counting by reconstructing hills and valleys of pulse trains.

FIG. 6 illustrates a flowchart 600 for photon counting by reconstructing hills and valleys of pulse trains. In step 610, signals are received indicating detected photons via a pulse shaper. In step 620, a plurality of pulses are generated therefrom to form a pulse train. In step 630, the pulse train is sampled at the output of the pulse shaper via a peak detector. In step 640, maximum and minimum values are selectively detected and sampled via a circuit in the peak detector. In step 650, the maximum and minimum values samples are converted from analog to digital format via an analog to digital converter. The process then ends for the first iteration.

Therefore, to summarize, a means is provided to reconstruct the correct pulse heights or even the full pulse train without sampling the analog shaper output at a very high sampling frequency. Since the shaper output results in "valley and hill" waveforms, in which the hills identify the pulse maximum, and the valleys represent a (possibly incomplete) return to the baseline, a circuit with an analog maximum detector and an analog minimum detector, both derived from a peak detector, is used to sample the pulse train at the output of the shaper, only at the maxima and minima. The sampled values are then analog-to-digitally converted via an ADC. Given the sequence of local maxima and minima (possibly with some timing information from a time counter), it is then possible to reconstruct the correct pulse heights or even the actual pulse train using a model for the shaper output, which can be obtained from test-pixel measurements or from CMOS circuit simulations. As a result a relatively accurate estimate of the complete pulse train is obtained, in which pile-up effects are visible, and hence can be corrected for.

It is to be appreciated that the embodiments described above may be used individually or in combination.

Applications also include luggage inspection, non-destructive testing, medical digital fluoroscopy, mammography, x-ray, as well as other industrial and medical applications.

The methods described herein may be implemented via one or more processors executing one or more computer readable instructions encoded or embodied on computer readable storage mediums, such as physical memory, which causes the one or more processors to carry out the various acts and/or other functions. The one or more processors can also execute instructions carried by transitory mediums, such as a signal or carrier wave.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An apparatus, comprising:
   a pulse shaper for receiving signals indicative of detected photons and generating a plurality of pulses therefrom to form a pulse train; and
   a peak detector for sampling the pulse train at an output of the pulse shaper, the peak detector including a circuit for selectively detecting and sampling a maximum value and a minimum value of the pulse train;
   an analog to digital converter that coverts the maximum value and the minimum value to a digital maximum value and a digital minimum value; and
   a time counter that generates a first value for a time clock tick during which the maximum or minimum is detected and a second value for a time clock tick during which the maximum or minimum is not detected;
   wherein the original pulse train is reconstructed using the digital maximum value, the digital minimum value, the first value, and the second value.

2. The apparatus of claim 1, wherein the peak detector samples only the maximum and minimum values.

3. The apparatus of claim 2, wherein the time counter detects a point in time for the maximum value and a point in time for the minimum value.

4. The apparatus of claim 3, wherein the point in time is recorded in a bit string format.

5. The apparatus of claim 1, wherein at least one pulse height of individual pulses of the plurality of pulses is reconstructed using the digital maximum value, the digital minimum value, the first value, and the second value.

6. The apparatus of claim 1, wherein the pulse train is reconstructed in its entirety via test-pixel measurements or CMOS circuit simulations.

7. The apparatus of claim 6, wherein a time counter detects a point in time for the maximum and minimum values.

8. The apparatus of claim 6, wherein the point in time is recorded in a bit string format.

9. The apparatus of claim 1, wherein at least some of the maximum and minimum values are subjected to buffering to accommodate phases of interarrival times.

10. The apparatus of claim 1, wherein the maximum and minimum values provide for an accurate estimate of pulse heights of the pulse train in which pile-up effects are determinable.

11. A method, comprising:
    receiving signals indicative of detected photons, via a pulse shaper;
    generating a plurality of pulses therefrom to form a pulse train;
    sampling the pulse train at an output of the pulse shaper, via a peak detector; and
    selectively detecting and sampling a maximum value and a minimum value of the pulse train, via a circuit in the peak detector;
    converting the maximum value and the minimum value to a digital maximum value and a digital minimum value;
    generating a first value for a time clock tick during which the maximum or minimum is detected;
    generating a second value for a time clock tick during which the maximum or minimum is not detected; and
    reconstructing the original pulse train using the digital maximum value, the digital minimum value, the first value, and the second value.

12. The method of claim 11, further including sampling only the maximum value and the minimum value.

13. The method of claim 12, further including detecting a point in time for the maximum and a point in time for the minimum values, via a time counter.

14. The method of claim 13, further including recording the point in time in a bit string format.

15. The method of claim 11, further including reconstructing at least one pulse height of individual pulses of the plurality of pulses using the digital maximum value, the digital minimum value, the first value, and the second value.

16. The method of claim 11, further including reconstructing the pulse train in its entirety via test-pixel measurements or CMOS circuit simulations.

17. The method of claim 16, further including detecting a point in time for the maximum and minimum values, via a time counter.

18. The method of claim 16, further including recording the point in time in a bit string format.

19. The method of claim 11, further including subjecting at least some of the maximum and minimum values to buffering to accommodate phases of interarrival times.

20. The method of claim 11, further including accurately estimating pulse heights of the pulse train in which pile-up effects are determinable, via the maximum and minimum values.

* * * * *